United States Patent [19]

Walker

[11] 4,216,222

[45] Aug. 5, 1980

[54] ALKYL OR ALKOXY-O-ALKYL-S-[N-(2-ALKYL, PHENYL OR VINYL-1,3-DIOXOLAN-4-YL) METHYLAMINOACETYL] DITHIOPHOSPHATES OR PHOSPHONATES AS INSECTICIDES AND ACARICIDES

[75] Inventor: Francis H. Walker, Mill Valley, Calif.

[73] Assignee: Stauffer Chemical Company, Westport, Conn.

[21] Appl. No.: 62,201

[22] Filed: Jul. 30, 1979

[51] Int. Cl.² .............................................. A01N 9/28
[52] U.S. Cl. ............................ 424/278; 260/340.9 R; 260/561 HL
[58] Field of Search ................. 260/340.9 R; 424/278

[56] References Cited

U.S. PATENT DOCUMENTS

| | | | |
|---|---|---|---|
| 3,247,223 | 4/1966 | Walsh et al. | 260/340.9 R |
| 3,317,561 | 5/1967 | Levy et al. | 260/340.9 R |
| 4,154,595 | 5/1979 | Walker | 260/340.9 R |

Primary Examiner—Ethel G. Love
Attorney, Agent, or Firm—Edwin H. Baker

[57] ABSTRACT

Compounds of the formula

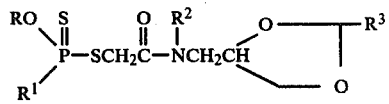

wherein R is alkyl having 1–5 carbon atoms; $R^1$ is alkyl having 1–4 carbon atoms, or alkoxy having 1–2 carbon atoms; $R^2$ is hydrogen or alkyl having 1–4 carbon atoms; and $R^3$ is alkyl having 1–4 carbon atoms, phenyl or alkenyl having 2–4 carbon atoms which are useful as insecticides and acaricides.

8 Claims, No Drawings

ALKYL OR ALKOXY-O-ALKYL-S-[N-(2-ALKYL, PHENYL OR VINYL-1,3-DIOXOLAN-4-YL) METHYLAMINOACETYL] DITHIOPHOSPHATES OR PHOSPHONATES AS INSECTICIDES AND ACARICIDES

DESCRIPTION OF THE INVENTION

This invention relates to certain novel chemical compounds and their use as insecticides and acaricides. More particularly, this invention relates to certain novel alkyl or alkoxy-O-alkyl-S-[N-(2-alkyl, phenyl or vinyl-1,3-dioxolan-4-yl)methylaminoacetyl]dithiophosphates or phosphonates which are useful as insecticides and acaricides.

The compounds of the present invention that are useful as insecticides and acaricides are those having the structural formula

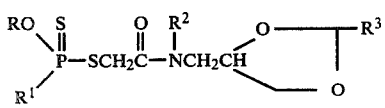

wherein R is alkyl having 1–5 carbon atoms; $R^1$ is alkyl having 1–4 carbon atoms, preferably methyl or ethyl, or alkoxy having 1–2 carbon atoms, preferably ethoxy; $R^2$ is hydrogen or alkyl having 1–4 carbon atoms, preferably hydrogen; and $R^3$ is alkyl having 1–4 carbon atoms, preferably methyl, phenyl or alkenyl having 2 to 4 carbon atoms, preferably vinyl.

In the above description of the compounds of this invention, alkyl includes both straight chain and branched chain configurations, for example, methyl, ethyl, n-propyl, isopropyl, n-butyl, iso-butyl or tert.butyl.

The compounds of the present invention are prepared by the following general method.

Reaction No. 1

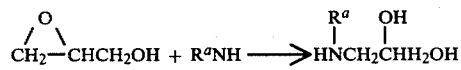

wherein $R^a$ is alkyl having 1–4 carbon atoms.

Generally, a mole amount of glycidol is reacted with a large excess, about 10 moles, of the alkylamine at a temperature of about 5°–10° C. with stirring for about one hour. The excess alkylamine is removed from the reaction mixture by evaporation under vacuum to yield the desired product.

Reaction No. 2

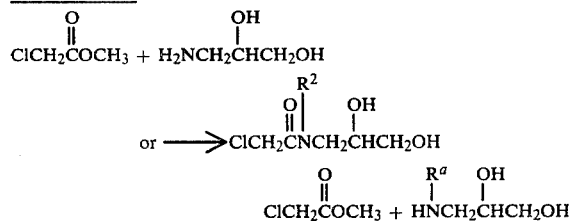

wherein $R^a$ is alkyl having 1–4 carbon atoms and $R^2$ is as defined.

Generally, a mole amount of 3-amino-1,2-propanediol dissolved in a solvent such as methanol is added to a solution of methyl chloroacetate in the same solvent at a temperature of about 5°–10° C. Then the reaction mixture is heated for about five hours at 5°–10° C. with stirring. Thereafter, the mixture is cooled and allowed to stand for several days. The solution is evaporated in vacuum to yield the desired product at high yields.

Reaction No. 3

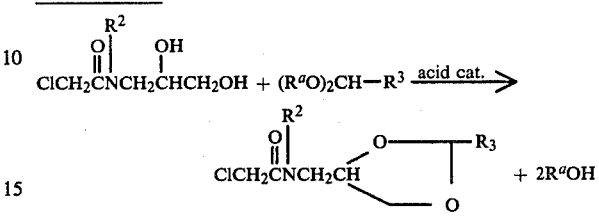

wherein $R^a$ is methyl or ethyl, $R^2$ and $R^3$ are as previously defined.

Generally, a mole amount of the amide reaction product of Reaction No. 1, a mole amount of the acetal reactant and about 0.2 mole of a strong acid catalyst such as 2-naphthalenesulfonic acid dihydrate or NH₄Cl or about one mole boron trifluoride etherate are dissolved in a solvent such as dichloroethane or acetonitrile mixed in a reaction vessel fitted with a packed distillation column, for example, a column packed with glass helices. The column is equipped with a variable tape-off distillation head attached to the column. The reaction mixture is heated to reflux with stirring. Initially, methyl or ethyl alcohol is removed as an azeotrope at its boiling temperature around 70°–73° C. for ethanol. When a head temperature reaches the boiling point of the solvent, 83° C., the reaction is complete.

The reaction mixture is then cooled to room temperature and washed with water, two portions of a base such as sodium carbonate solution and finally water. The final aqueous solution is dried over magnesium sulfate and evaporated to yield the desired reaction product.

The acetal reactant, $(R^aO)_2CH-R^3$, where $R^a$ and $R^3$ are as defined, can be prepared in situ if desired by reacting either trimethylorthoformate or triethylorthoformate with the appropriately substituted acetaldehyde.

Reaction No. 4

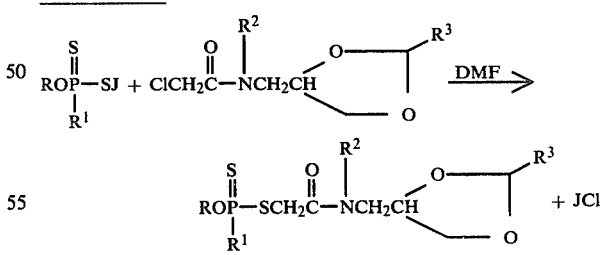

wherein R, $R^1$, $R^2$ and $R^3$ are as defined and J is potassium or ammonium.

Generally, a slight excess of the potassium salt of the dithioyl phosphate or phosphonate and the chloroacetamide are stirred together in dimethyl formamide as a solvent first at room temperature for about four hours and then at about 50° C. for an additional four hours. At the end of this time, the mixture is diluted with toluene, washed with a brine solution, dried and evaporated to yield the desired reaction product.

Preparation of the compounds of this invention is illustrated by the following examples.

EXAMPLE I

N-(2,3-dihydroxypropyl)chloroacetamide

This example teaches a method of preparation for the reactant N-(2,3-dihydroxypropyl)chloroacetamide.

A solution of 25 grams (g) (0.27 mole) of 3-amino-1,2-propanediol in 50 milliliter (ml) methyl alcohol is added slowly to a solution of methyl chloroacetate, 33.0 g (0.30 mole) in 50 ml methyl alcohol at 5°–10° C. The solution is stirred for five hours at 5°–10° C. and is then allowed to stand in the cold for four days. The solution is then evaporated in vacuum to leave 43 g of the desired product, a viscous oil, $n_D^{30}$ 1.5148. (95% yield).

EXAMPLE II 2-phenyl-4-(chloroacetylamino)methyl-1,3-dioxolane

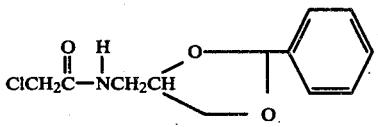

This examples teaches the preparation of an intermediate compound.

A mixture of 60 g (0.04 mole) of N-(2,3-dihydroxypropyl) chloroacetamide, 7.2 g (0.04 mole) of benzaldehyde diethylacetal and 0.2 g 2-naphthalenesulfonic acid dihydrate.

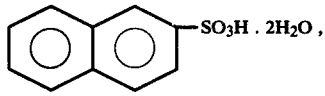

in 50 ml dichloroethane are placed in a 100 ml flask fitted with a magnetic stirring bar, thermometer and a 10 centimeter (cm) column packed with glass helices. A variable tape-off distillation head is attached to the column. The reaction mixture is heated to reflux in this apparatus and the formed ethyl alcohol is removed as an azeotrope at a temperature of about 70°–73° C. Distillate is removed until a head temperature of 83° C. is reached to give 7.1 g.

The reaction mixture is then cooled to room temperature and washed with 50 ml water, two 50 ml portions of sodium carbonate solution and 50 ml water. The solution is dried over magnesium sulfate and evaporated to yield the desired product, a liquid 5.8 g (63% yield), $n_D^{30}$ 1.5428, identified as the title compound by nuclear magnetic resonance and mass spectroscopy.

EXAMPLE 3

O,O-dimethyl-S-[N-(2-phenyl-1,3-dioxolane-4-yl]methyl amino acetyl dithiophosphate

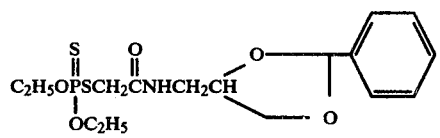

This example teaches the synthesis of a compound of this invention.

2.4 g (0.012 mole) ammonium salt of diethyldithiophosphate and 50 ml dimethylformamide were added to a 200 ml round bottom flask equipped with a magnetic stirrer and thermometer. 3.1 g (0.012 mole) of the dioxolane compound prepared in Example II was added and the mixture stirred for 12 hours. The reaction product was taken up in 100 ml toluene and washed three times with brine. The organic phase was dried with MgSO₄, filtered and the solvent removed in a rotary vacuum, yielding 3.7 g of the desired compound $n_D^{30}$ 1.5534. The structure was confirmed by nuclear magnetic resonance and mass spectroscopy.

The following is a table of certain selected compounds that are preparable according to the presence described hereto. Compound numbers are assigned to each compound and are used through the remainder of the application.

Table 1

$$\underset{R^1}{\overset{RO}{>}}\overset{S}{\underset{\|}{P}}-SCH_2\overset{O}{\underset{\|}{C}}-N\underset{|}{\overset{R^2}{|}}CH_2CH\overset{O}{\underset{O}{\diagdown}}R^3$$

| Compound Number | R | R¹ | R² | R³ | $n_D^{30}$ or m.p. |
|---|---|---|---|---|---|
| 1 | C₂H₅— | C₂H₅— | —H | —CH₃ | 1.5309 |
| 2 | C₂H₅— | C₂H₅— | —H | —CH(CH₃)₂ | 1.5238 |
| 3 | C₂H₅— | C₂H₅— | —H | —C₆H₅ (phenyl) | 1.5604 |
| 4 | C₂H₅— | C₂H₅— | —H | —CH₂CH₂CH₃ | 1.523 |
| 5 | C₂H₅— | C₂H₅— | —H | —C₂H₅ | 1.529 |
| 6 | C₂H₅— | C₂H₅— | —H | —CH=CH₂ | 1.532 |
| 7 | C₂H₅— | C₂H₅— | —H | —CH(CH₃)CH₃ | 1.5265 |
| 8 | CH₃CH(CH₃)— | C₂H₅— | —H | —CH₃ | 1.5272 |

Table 1-continued $$RO\underset{R^1}{\overset{S}{\underset{\|}{P}}}-SCH_2\overset{O}{\underset{\|}{C}}-\underset{R^2}{\overset{|}{N}}CH_2CH\overset{O-}{\underset{O}{\diagdown}}R^3$$

| Compound Number | R | $R^1$ | $R^2$ | $R^3$ | $n_D^{30}$ or m.p. |
|---|---|---|---|---|---|
| 9 | CH₃CHCH₂—<br>\|<br>CH₃ | C₂H₅— | —H | —CH₃ | 1.5238 |
| 10 | (CH₃)₃C— | C₂H₅— | —H | —CH₃ | 1.554 |
| 11 | (CH₃)₂CHCH₂CH₂— | C₂H₅— | —H | —CH₃ | 1.5210 |
| 12 | C₂H₅— | OC₂H₅— | —H | —CH₃ | 1.5196 |
| 13 | CH₃— | CH₃O— | —H | —CH₃ | 1.5277 |
| 14 | C₂H₅— | C₂H₅O— | —H | —CH₃ | 1.5205 |
| 15* | C₂H₅— | C₂H₅O— | —H | —C₆H₅ (phenyl) | 1.5534 |
| 16 | C₂H₅— | C₂H₅— | —CH₂CH₂CH₃ | —CH₃ | 1.5210 |
| 17 | C₂H₅— | C₂H₅O— | —CH₂CH₂CH₃ | —CH₃ | 1.5067 |

*Prepared in Example III.

Insecticidal Evaluation Tests

The compounds of Table I were found to have insecticidal activity against the following insect species which were used in the evaluation tests described hereafter.

1. Housefly (HF)—*Musca domestica* (Linn.)
2. Black Bean Aphid (BBA)—*Aphis fabae* (Scop.)
3. Green Peach Aphid (GPA)—*Myzus persicae* (Sulzer)

The insecticidal evaluation tests were conducted as follows:

Housefly: Test compounds were diluted in acetone and aliquots pipetted onto the bottom of 55×15 mm aluminum dishes. To insure even spreading of the chemical on the bottom of the dishes, one ml of acetone containing 0.02% peanut oil was also added to each dish. After all solvents had evaporated, the dishes were placed in circular cardboard cages containing 25 female houseflies, one to two days old. The cages were covered on the bottom with cellophane and on top with tulle netting, and each contained a sugar-water saturated cotton plug for maintenance of the flies. Mortality was recorded after 48 hours. Test levels ranged from 100 μg/25 female houseflies down to that at which approximately 50% mortality occurred. The LD₅₀ values are expressed below in Table II under the heading "HF", in terms of μg of the test compound per 25 female flies.

Black Bean Aphid: Nasturtium plants (Tropaeolum sp.), approximately five cm tall, were transplanted into sandy loam soil in three-inch clay pots and infested with 25–50 black bean aphids of mixed ages. Twenty-four hours later they were sprayed to the point of runoff with 50–50 acetone-water solutions of the test chemicals. Treated plants were held in the greenhouse and mortality was recorded after 48 hours. Test concentrations ranged from 0.05% down to that at which 50% mortality occurred. LD₅₀ values are expressed below in Table II under the heading "BBA" in terms of percent of the test compound in the sprayed solution.

Green Peach Aphid: Radish plants (*Rhaphanus sativus*), approximately two cm tall, were transplanted into sandy loam soil in three-inch clay pots and infested with 25–50 green peach aphids of mixed ages. Twenty-four hours later they were sprayed to the point of runoff whith 50—50 acetone-water solutions of the test chemicals. Treated plants were held in the greenhouse and mortality was recorded after 48 hours. Test concentrations ranged from 0.05% down to that at which 50% mortality occurred. LD₅₀ values are expressed below in Table II under the heading "GPA" in terms of percent of the test compound in the sprayed solution.

Acaricidal Evaluation Test

The twp-spotted mite (2SM), *Tetranychus urticae* (Koch), was employed in tests for miticides. The test procedure was as follows:

Pinto bean plants (Phaseolus sp.), approximately 10 cm. tall, were transplanted into sandy loam soil in three-inch clay pots and thoroughly infested with two-spotted mites of mixed ages and sexes. Twenty-four hours later, the infested plants were inverted and dipped for two-three seconds in 50—50 acetone-water solutions of the test chemicals. Treated plants were held in the greenhouse, and seven days later mortality was determined for both the adult mites and the nymphs hatching from eggs which were on the plants at the time of treatment. Test concentrations ranged from 0.05% down to that at which 50% mortality occurred. LD₅₀ values are expressed below in Table II under the headings "2SM-PE" (i.e., post-embryonic) and "2SM-Eggs", in terms of percent concentration of the test compound in the solution.

Table II

| Compound Number | HF (μg) | BBA (%) | GPA (%) | 2SM-PE (%) | 2SM-EGGS |
|---|---|---|---|---|---|
| 1 | 60 | .0006 | .0003 | .008 | .008 |
| 2 | 37 | .0007 | .003 | .01 | .003 |
| 3 | 54 | .001 | .001 | ** | .05 |
| 4 | 30 | .0002 | .0003 | .003 | .03 |
| 5 | 32 | .0002 | .002 | .008 | .03 |
| 6 | 50 | .0005 | .002 | .008 | ** |
| 7 | 24 | .0005 | .001 | .008 | .03 |
| 8 | 100 | .0002 | .0005 | .001 | .008 |
| 9 | 34 | .001 | .0005 | .001 | .008 |
| 10 | 75 | .003 | .005 | .003 | .03 |
| 11 | 65 | .001 | .0005 | .001 | .008 |
| 12 | * | .003 | .03 | .008 | ** |
| 13 | * | .002 | .03 | .008 | ** |
| 14 | 89 | .005 | .03 | .003 | .05 |
| 15 | * | .03 | .03 | .01 | .03 |
| 16 | 32 | .0003 | .0002 | .008 | .008 |

Table II-continued

| Compound Number | HF (μg) | BBA (%) | GPA (%) | 2SM-PE (%) | 2SM-EGGS (%) |
|---|---|---|---|---|---|
| 17 | 48 | .008 | .005 | .03 | .05 |

\* = Not active at 100 μg and not tested at higher concentrations.
\*\* = Not active at 0.05% and not tested at higher concentrations.

The compounds of this invention are generally formulated into a form suitable for convention application. For example, the compounds can be prepared into a pesticidal composition in the form of emulsions, suspensions, solutions, dusts or aerosol sprays. In general, such pesticidal compositions will contain, in addition to the active compound, the inert adjuvants which are found normally in pesticide preparations. In these compositions, an active compound of the invention can be employed as the sole pesticide component or it can be used in an admixture with other compounds having similar utility.

The pesticide compositions of this invention can contain, (a) liquid adjuvants, such as organic solvents, sesame oil, xylene range solvents, heavy petroleum, etc.; water; (b) emulsifying agents; (c) surface active agents; (d) solid adjuvants such as talc; pyrophyllite, diatomite; gypsum; clays or (e) propellants, such as dichlorodifluoromethane, etc.

If desired, however, the active compounds can be applied directly to feedstuffs, seeds, etc., or upon other materials upon which the pests feed. In connection with the activity of the presently disclosed pesticidal compounds, it should be fully understood that it is not necessary that they be active as such. The purposes of this invention will be fully served if the compound is rendered active by external influences, such as light or by some physiological action which occurs when the compound is ingested into the body of the pest.

The precise manner in which the pesticidal compositions of this invention are used in any particular instance will be readily apparent to a person skilled in the art. Generally, the active pesticide compound will be embodied in the form of a liquid composition; for example, an emulsion, suspension, or aerosol spray. While the concentration of the active compound in the aforesaid compositions can vary within wide limits, ordinarily the active compound will comprise between about 1.0 and about 95% by weight of the pesticidal composition and more preferably between about 5%-80% by weight.

I claim:

1. Compounds having the structural formula

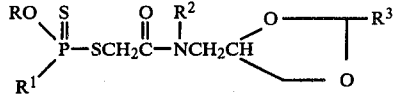

wherein R is alkyl having 1–5 carbon atoms; $R^1$ is alkyl having 1–4 carbon atoms, or alkoxy having 1–2 carbon atoms; $R^2$ is hydrogen or alkyl having 1–4 carbon atoms; and $R^3$ is alkyl having 1–4 carbon atoms, phenyl or alkenyl having 2 to 4 carbon atoms.

2. A compound according to claim 1 wherein R is ethyl, $R^1$ is ethyl, $R^2$ is hydrogen and $R^3$ is isopropyl.

3. A compound according to claim 1 wherein R is ethyl, $R^1$ is ethyl, $R^2$ is hydrogen and $R^3$ is n-propyl.

4. A compound according to claim 1 wherein R is ethyl, $R^1$ is ethyl, $R^2$ is hydrogen and $R^3$ is di-methyl.

5. A compound according to claim 1 wherein R is isobutyl, $R^1$ is ethyl, $R^2$ is hydrogen and $R^3$ is methyl.

6. A compound according to claim 1 wherein R is ethyl, $R^1$ is ethyl, $R^2$ is n-propyl and $R^3$ is methyl.

7. The method of controlling insects comprising applying to the habitat thereof an insecticidally effective amount of a compound of the formula

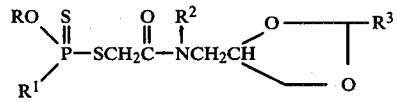

wherein R is alkyl having 1–5 carbon atoms; $R^1$ is alkyl having 1–4 carbon atoms, or alkoxy having 1–2 carbon atoms; $R^2$ is hydrogen or alkyl having 1–4 carbon atoms; and $R^3$ is alkyl having 1–4 carbon atoms, phenyl or alkenyl having 2–4 carbon atoms.

8. The pesticidal composition comprising a pesticidally effective amount of a compound of the formula

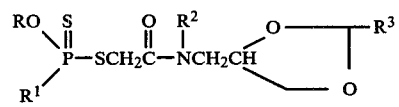

wherein R is alkyl having 1–5 carbon atoms; $R^1$ and is alkyl having 1–4 carbon atoms, or alkoxy having 1–2 carbon atoms; $R^2$ is hydrogen or alkyl having 1–4 carbon atoms; and $R^3$ is alkyl having 1–4 carbon atoms, phenyl or alkenyl having 2–4 carbon atoms and an inert carrier therefor.

* * * * *